(12) United States Patent
Chang et al.

(10) Patent No.: US 7,501,250 B2
(45) Date of Patent: Mar. 10, 2009

(54) BLOTTING METHOD FOR RAPIDLY ANALYZING NUCLEIC ACID

(76) Inventors: Chung-Cheng Chang, No. 2, Pei-Ning Road, Keelung (TW) 20224; Jau-Der Chen, No. 2, Pei-Ning Road, Keelung (TW) 20224; Pei-Tai Chen, No. 2, Pei-Ning Road, Keelung (TW) 20224

( * ) Notice: Subject to any disclaimer, the term of this patent is extended or adjusted under 35 U.S.C. 154(b) by 0 days.

(21) Appl. No.: 11/535,478

(22) Filed: Sep. 26, 2006

(65) Prior Publication Data

US 2008/0076125 A1    Mar. 27, 2008

(51) Int. Cl.
 *C12Q 1/68* (2006.01)
 *C07H 21/02* (2006.01)
 *C07H 21/04* (2006.01)
(52) U.S. Cl. .................... 435/6; 536/23.1; 536/24.3
(58) Field of Classification Search ............... 435/6; 536/23.1, 24.3
   See application file for complete search history.

(56) References Cited

U.S. PATENT DOCUMENTS

| | | | |
|---|---|---|---|
| 5,468,632 A * | 11/1995 | Cantwell et al. | 435/479 |
| 5,663,318 A * | 9/1997 | Pegg et al. | 536/24.3 |
| 5,831,102 A * | 11/1998 | Bronstein et al. | 549/332 |
| 5,843,647 A * | 12/1998 | Jeffreys et al. | 435/6 |
| 6,174,677 B1 * | 1/2001 | Vo-Dinh | 435/6 |
| 6,528,484 B1 * | 3/2003 | Ensign et al. | 514/12 |
| 6,638,760 B1 * | 10/2003 | Chen et al. | 435/287.2 |
| 6,927,322 B2 * | 8/2005 | Stewart et al. | 800/302 |
| 2004/0014043 A1 * | 1/2004 | Levison et al. | 435/6 |
| 2004/0157320 A1 * | 8/2004 | Andreoli et al. | 435/287.2 |
| 2005/0164188 A1 * | 7/2005 | Kane | 435/6 |
| 2006/0134119 A1 * | 6/2006 | Hirashima et al. | 424/155.1 |
| 2006/0134397 A1 * | 6/2006 | Smith | 428/304.4 |
| 2007/0148783 A1 * | 6/2007 | Solomon et al. | 436/518 |

OTHER PUBLICATIONS

Product Details for Gene Sceen Plus obtained from perkinelmer.com. One page.*
Zhang et al., Single-base mutational analysis of cancer and genetic diseases using membrane bound modified oligonucleotides. Nucleic Acids Research 19 (14) : 3929-3933 (1991).*
Davis et al., Basic Methods in Molecular Biology, pp. 62-65 and 80-87 (1991).*
ECL Direct Nucleic Acid Labelling and Detecting Systems. Product Booklet. pp. 1-55 Copyright 2006.*

* cited by examiner

*Primary Examiner*—Ethan Whisenant
(74) *Attorney, Agent, or Firm*—WPAT, P.C.; Anthony King

(57) ABSTRACT

The present invention relates to a blotting method for rapidly analyzing nucleic acid comprising the steps of transferring a nucleic acid to be analyzed to the substrate and fixing the nucleic acid to be analyzed absorbed on the substrate; directing adding a nucleic acid probe to hybridize in a short time, without blocking the areas where the nucleic acid to be analyzed has not been fixed; removing the nucleic acid probe which has not been annealed to the nucleic acid to be analyzed by washing; and finally detecting the hybridization signal. According to the present invention, since the prehybridization is not needed and the hybridization and washing time is shortened, the time for the nucleic acid hybridization is dramatically shortened. Therefore, the whole blotting procedures for rapidly analyzing nucleic acid may be finished quickly.

16 Claims, 6 Drawing Sheets

BLOTTING METHOD FOR RAPIDLY ANALYZING NUCLEIC ACID

BACKGROUND OF THE INVENTION

1. Technical Field

The present invention relates to a method for analyzing nucleic acid, specially to a blotting method for rapidly analyzing nucleic acid in which the nucleic acid to be analyzed is directly transferred to a substrate, and the time for nucleic acid hybridization is shortened.

2. Technical Background

In the conventional gene cloning, in order to determine whether the gene or DNA fragment is correctly cloned in the carrier, the gel electrophoresis may be performed to analyze the molecular weight of the DNA. In addition, another more precise means is by hybridizing a nucleic acid probe with the DNA to be determined to analyze whether the DNA to be determined comprises the desired gene or DNA fragment. Likewise, in order to study the gene expression, the length and expression amount of mRNA generated after transcription, is required to be detected after the expression of gene, by hybridizing a nucleic acid probe with the RNA and then analyzing the length or copy number of the RNA.

A blotting method generally comprises the steps of absorbing the nucleic acid to be analyzed on a membrane, hybridizing and pairing the nucleic acid with a probe having specificity, and then presenting the result of the hybridization by the probe-marked present molecule in a presenting method such as coloring method, chemiluminescence method, radiography method and so on. The nucleic acid to be analyzed may be absorbed on the membrane by transferring from electrophoresis gel or directly dropping the nucleic acid to be analyzed on the membrane to make the nucleic acid penetrated therein. A blotting method in which a DNA sample transferred to the membrane by electrophoresis gel is hybridized with the probe is referred to as Southern blotting method. A blotting method in which a RNA sample transferred is hybridized is referred to as Northern blotting method. A blotting method in which the nucleic acid to be analyzed is directly dropped is referred to as dot-/slot-/spot blotting method according to the dropping area. The dot-/slot-/spot blotting method is usually applied in qualitative analysis or scores of analysis, because the analyzing time can be shortened due to the needlessness of electrophoresis for separation and transfer, and the cost is low due to the needlessness of electrophoresis and transferring devises and related agents.

Referring to FIG. 1, it is a flow chart showing the known dot blotting method. The whole blotting method comprises pretreatment of the membrane (step S10), treatment of the nucleic acid to be analyzed (step S20), hybridization of the nucleic acid (step S30) and detection of the hybridization signal (step S40). The membrane is firstly treated, the nucleic acid to be analyzed is dropped thereon, the nucleic acid is hybridized with a probe, and finally the hybridization signal is detected to finish the whole procedure of dot blotting.

The membrane pretreatment in step S10 comprises providing a membrane able to absorb the nucleic acid to be analyzed (step S11), and then soaking the membrane (step S12) to make the membrane be wet to further penetrate and absorb the nucleic acid to be analyzed. Currently conventional membrane includes nylon membrane and nitrocellulose membrane which is soaked completely in deionized water and then in 6 to 10 folds standard sodium citrate (SSC) for use, wherein 20 folds SSC comprises 3 M sodium chloride and 0.3 M sodium citrate of pH 7.0.

Prior to the hybridization, either DNA sample or RNA sample has to be subjected to denaturation to keep itself in a state of single chain, in order to pair with the probe of single chain. Accordingly, during treatment of the nucleic acid to be analyzed in step S20, the nucleic acid is prepared in step S21, denatured in step S22, and then dropped on the membrane in step S23. After being absorbed on the membrane, the nucleic acid to be analyzed is fixed thereon to prevent it from falling off in the subsequent hybridization process. The known fixing method for nucleic acid is to dry for 30 minutes to 2 hours at 80° C. in step S24, or to radiate with ultraviolet at 254 nm to form covalent crosslinkage between the nucleic acid molecules and cellulose of the membrane to fix the nucleic acid molecules thereon in step S25.

After being fixed on the membrane, the nucleic acid to be analyzed is then hybridized in step S30. The nucleic acid to be analyzed has not been fixed on some areas of the membrane where the nucleic acid can be still absorbed, and if these areas are not blocked, the added probe which is also nucleic acid will be non-specifically bonded to these areas of the membrane. Accordingly, prior to the hybridization, the step of prehybridization S31 has to be performed by adding a solution containing 5 folds SSC solution, 50% (v/v) formamide, 0.1% (w/v) sodium dodecyl sulfate (SDS) solution and 5% casein on the membrane and reacting them for 1 to 2 hours at 42° C. to block the areas where the nucleic acid to be analyzed has not been fixed.

Subsequently, in the hybridization step S32, the nucleic acid probe marked with enzyme or radioactive elements is added on the membrane having been subjected to the prehybridization, and is then reacted for more than 16 hours at 42° C. During this course, the probe can find and pair with the complementary nucleic acid to be analyzed. Then, in the washing step S33, the nucleic acid probe that is not paired will be washed off. During washing, a washing solution containing 2 folds SSC solution and 0.1% (w/v) SDS is used to wash twice at the ambient temperature and for 5 minutes each time. And then a washing solution containing 0.1 fold SSC solution and 0.1% (w/v) SDS is used to wash twice at 68° C. and for 15 minutes each time.

After the washing step S33, only the probes pairing with the nucleic acid to be analyzed remain on the membrane, and at this time the detection step S40 can be performed to detect the hybridization signal. A suitable detection method may be used to detect the hybridization signal according to the detecting molecules marked with the probe. The conventional detection method includes color reaction detection method S41 using the digoxigenin (DIG) system, radiography detection method S42 marking the radioactive element $^{32}P$ or $^{35}S$, and chemiluminescence detection method S43 using HEX, Cy3 and Cy5.

It could be seen from the above steps that, in the known blotting method, it takes many procedures and long time to finish the membrane pretreatment (step S10), treatment of the nucleic acid to be analyzed (step S20), and hybridization of the nucleic acid (step S30), and it will take about 2 days to finish all the procedures including the detection of the hybridization signal (step S40). Such that the experiments of which the result is urgent to get can not be finished in a short time. In addition, if a lot of time and agents should be also used for some simple qualitative test of nucleic acid, the method will be not economical. Accordingly, it is required to develop a rapid blotting method in which the time and procedures for blotting analysis can be shortened and the background noise can be lowered. For either the simple test or scores of tests, the experiment time can be effectively shortened, and at the same time the cost of the consumed materials can be largely lowered.

SUMMARY OF THE INVENTION

In order to simplify the procedures of the blotting method, reduce the experiment time, agents and solutions, and shorten the time for the entire analysis, the present invention provides a blotting method for rapidly analyzing nucleic acid in which the known steps such as the prehybridization is not needed, and the time for nucleic acid blotting analysis can be largely shortened. According to the blotting method for rapidly analyzing nucleic acid of the present invention, the blocking required for the known prehybridization is not needed, and the time for pairing the nucleic acid probe with the nucleic acid to be analyzed and washing can be correspondingly shortened by using the ability of bases to pair in very short time, so the time for the entire blotting method can be largely shortened, and the procedures from the treatment of the nucleic acid to be analyzed to the hybridization of the nucleic acid can be finished in tens of minutes. The object to save experiment time and reduce the cost of the related agents and solutions is achieved.

The blotting method for rapidly analyzing nucleic acid of the present invention comprises the following steps: (1) providing a substrate having a plurality of pores; (2) transferring a nucleic acid to be analyzed to the substrate and making the nucleic acid to be analyzed absorbed by the substrate; (3) fixing the nucleic acid to be analyzed on the substrate; (4) adding a solution containing a nucleic acid probe on the substrate of step (3) to base-pair the nucleic acid probe with the nucleic acid to be analyzed thereon for several minutes, without blocking the areas of the substrate where the nucleic acid to be analyzed has not been fixed; (5) removing the nucleic acid probe which has not been annealed to the nucleic acid to be analyzed of step (4); and (6) detecting the hybridization signal on the substrate having been subjected to step (5).

In step (1), the substrate may be membranes, silicone chips, glass, magnetic beads and metal particles, but is not limited thereto. Therefore, after being transferred to the substrate, the nucleic acid to be analyzed may be absorbed on the substrate in step (2) and step (3) in a manner of the dry absorbing, the electric absorbing, the magnetic absorbing and so on, but the absorbing method is not limited thereto. In the subsequent step (4), the nucleic acid to be analyzed may be fixed on the substrate in the means of desiccation, heat drying, ultraviolet radiation, or magnetic absorbing, and the fixing method is also not limited to the above-mentioned ones. The nucleic acid probe which is not paired can be removed because of the characteristics of the hydrogen bond to quickly pairing linkage, so that the time for the probe to absorb on the membrane is too short, such that part of steps required for known hybridization is not needed, and the long latency time required for the reaction can be shortened.

At the same time, the present invention provides another blotting method for rapidly analyzing nucleic acid comprising the following steps: (1) providing a membrane that may be dry; (2) transferring a nucleic acid to be analyzed to the membrane and making the nucleic acid to be analyzed absorbed by the membrane; (3) fixing the nucleic acid to be analyzed on the membrane, and then drying the membrane; (4) interacting a solution containing a nucleic acid probe with the membrane of step (3) at a temperature of 40° C. to 70° C. to base-pair the nucleic acid probe with the nucleic acid to be analyzed thereon for 2 to 5 minutes, without blocking the areas of the substrate where the nucleic acid to be analyzed has not been fixed; (5) washing the membrane of step (4) with a buffer solution to remove the nucleic acid probe which has not been annealed to the nucleic acid to be analyzed; and (6) detecting the hybridization signal on the membrane having been subjected to step (5).

The nucleic acid sample to be analyzed in the present invention may be DNA or RNA, and the membrane of step (1) may be, but not limited to, a nylon membrane or a nitrocellulose membrane. The nylon membrane may have positive charge or have no charge. The pores of the nylon membrane and nitrocellulose membrane may have a diameter of 0.1 to 50 µm, and preferably 0.2 to 0.45 µm. A diameter may be suitably selected according to the molecular weight of the nucleic acid to be analyzed, and becomes larger as the nucleic acid is larger. In addition, the membrane may not need the pretreatment of soaking, and be dry in order to rapidly absorb the nucleic acid to be analyzed on the membrane upon dropping it thereon. In step (3), the membrane having absorbed the nucleic acid to be analyzed may be dried at a temperature of 80° C. to 130° C., preferably 100° C. to 120° C., for 1 to 10 minutes to fix the nucleic acid to be analyzed on the membrane. Alternatively, the nucleic acid to be analyzed may also be fixed on the membrane by radiating with ultraviolet, and then the membrane may be further desiccated by drying. The buffer solution of step (5) preferably has a low ionic strength, and may include the standard sodium citrate solution of 0.05 to 0.15 fold, preferably 0.1 fold, and sodium dodecyl sulfate solution of 0.05% to 0.15(w/v), preferably 0.1(w/v). The washing time may be 3 to 6 minutes.

According to the blotting method for rapidly analyzing the nucleic acid, the pretreatment differs from the known one in that the nucleic acid to be analyzed is directly dropped on a dry membrane to be absorbed thereon, while not firstly soaking the membrane and then drying it for fixation. Since the nucleic acid spreads more quickly on a dry membrane than on a wet one, the nucleic acid to be analyzed can be quickly absorbed by the membrane, and thus the time for the pretreatment of the membrane can be shortened and the device, solution and agents required for the related procedures can also be saved.

After the nucleic acid to be analyzed is dropped and fixed on the membrane, the membrane may be desiccated by drying, and then the hybridization can be performed. In the known analysis, it is required to block the areas of the where the nucleic acid to be analyzed has not been fixed with a solution containing a blocking reagent, to prevent the non-specific bond of the probe. However, in the present method, the prehybridization is not needed, the nucleic acid probe is directly added on the membrane for hybridization, and the hybridization process can be finished in several minutes. This is because that, when being added on a dry membrane compared with a wet one, the nucleic acid probe solution can be quickly attracted by the capillarity generated by the fine pores of the membrane, and thus can be quickly absorbed by the membrane and enter the pores therein. The nucleic acid in the nucleic acid probe solution moves in the membrane in the manner of Brown Movement, and synchronously finds the complementary nucleic acid to be analyzed. For example, when a DNA having 30 nucleotides (30-mer) moves in a 5 µm pore of the membrane, the diffusing time is only 0.6 second, while still just 25 seconds for a 5000-mer DNA. At the same time, according to the well-known Polymerase chain reaction (PCR), the time for annealing the primer to the sample nucleic acid is less than 1 minute. Accordingly, in the present invention, the nucleic acid probe can finish the base pairing in rather a short time, and thus the hybridization time can be shortened from tens of hours to several minutes.

On the other hand, as described above, the nucleic acid probe pairs with the nucleic acid to be analyzed by the binding force of the purine or pyrimidine hydrogen bond, and compared with the absorbing speed of the nucleic acid probe on the membrane, the hydrogen bond is formed more quickly. The bonding force between the nucleic acid probe is stronger than the absorbing force between the nucleic acid probe and the membrane, and the absorbing force between the nucleic acid to be analyzed is stronger than that between the nucleic acid probe and the membrane. Moreover, unlike the giant molecule of the nucleic acid to be analyzed, the nucleic acid probe as a relatively small molecule can not be blocked in the pores of the membrane, and thus the nucleic acid probe which is non-specifically bonded to the membrane can be easily to remove in the subsequent washing, resulting in the hybridization of low background noise. The above is the reason that the prehybridization blocking is not needed. However, in order to prevent nucleic acid to be analyzed having been fixed from being removed during washing, it is preferred to wash with a buffer solution of low ionic strength for several minutes, preferably 4 to 6 minutes.

After washing, the hybridized membrane will be subjected to the detection of the hybridization signal by the currently known method or kit. It may also be done by a photoelectric detection method to shorten the detection time to several minutes. The photoelectric detection method includes and is not limited to impedance detection, capacitance detection, resistance detection, and electrochemical detection.

In conclusion, according to the blotting method for rapidly analyzing nucleic acid of the present invention, either the treatment of the nucleic acid to be analyzed from step (1) to step (3) or the nucleic acid hybridization from step (4) to step (5) can be finished in several minutes, the time for all the above steps is just 15 to 30 minutes, and thus the time and material cost of the blotting method for analyzing the nucleic acid is largely and efficiently improved compared with the traditional method.

Hereinafter, the embodiments of the present invention will be further described with regard to the drawings. The following examples are provided only in purpose of demonstration and can not be construed to limit the scope of the present invention. It is apparent for the skilled in this art to make any change or modification within the scope and spirit of the invention, and the scope of the present invention will be defined by the appended claims.

PREFERRED EMBODIMENT OF THE INVENTION

Figure 2:
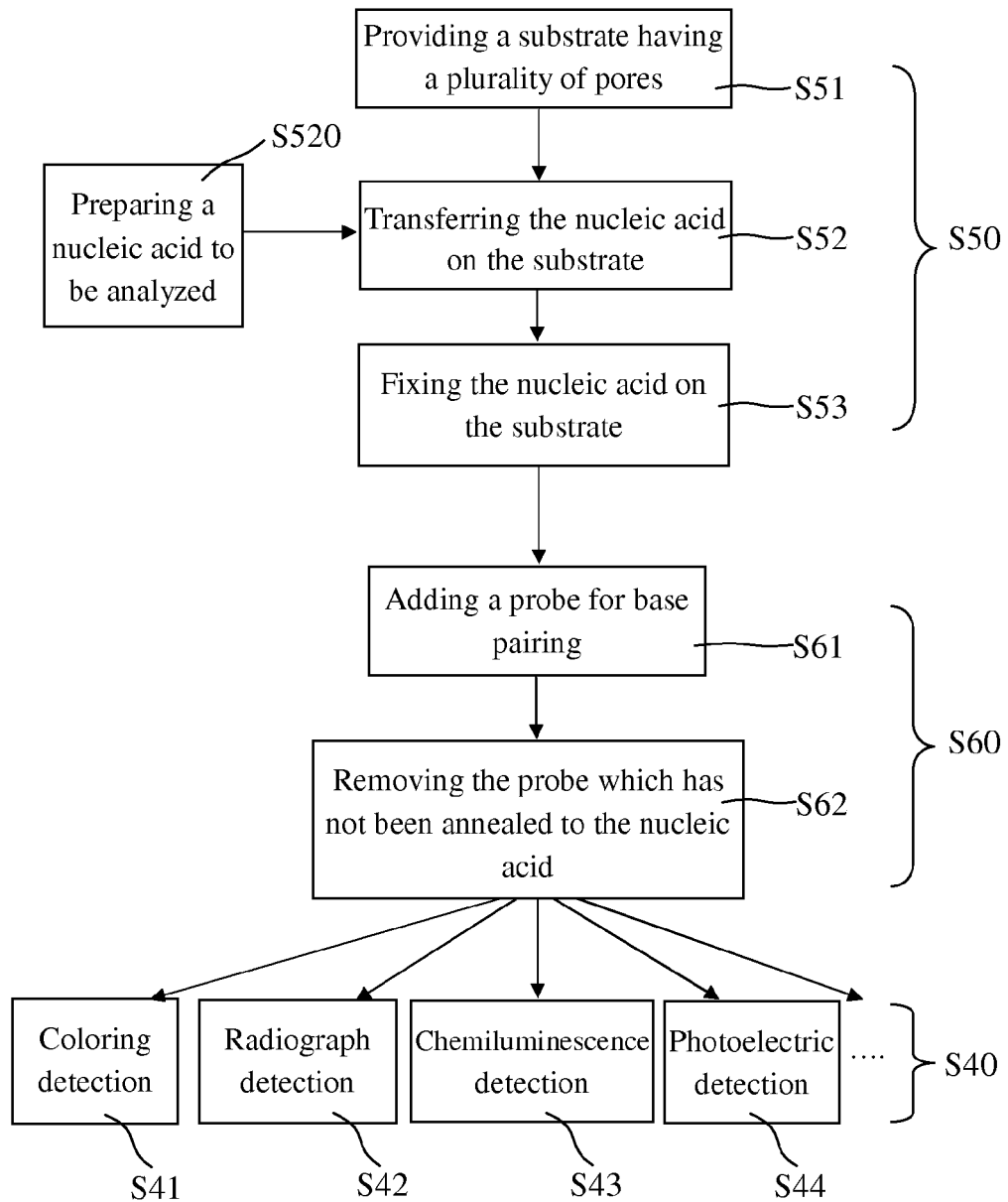
FIG. 2 is a flow chart showing one embodiment of the present invention.

Referring to FIG. 2 which is a flow chart showing one embodiment of the present invention, the blotting method for rapidly analyzing nucleic acid according to the embodiment of the present invention includes the steps of the treatment of the nucleic acid to be analyzed S50, the hybridization of the nucleic acid S60 and the detection of the hybridization signal S40. The nucleic acid to be analyzed is firstly transferred to the substrate, fixed thereon, and hybridized and paired without the step of prehybridization, and finally the hybridization signal is detected to finish the procedures of the blotting method for analyzing the nucleic acid of the present invention.

Also referring to FIG. 2, the treatment of the nucleic acid to be analyzed (step S50) includes providing a substrate having a plurality of pores in step S51; transferring a nucleic acid to be analyzed which is prepared in step S520 to the substrate and making the nucleic acid to be analyzed absorbed by the substrate in step S52; fixing the nucleic acid to be analyzed on the substrate in step S53. In step S51, the substrate may be membranes, silicone chips, glass, magnetic beads and metal particles, but is not limited thereto. Therefore, after being transferred to the substrate, the nucleic acid to be analyzed may be absorbed on the substrate in steps S52 and S53 in a manner of the dry absorbing, the electric absorbing, the magnetic absorbing and so on, but the absorbing method is not limited to.

After the treatment of the nucleic acid to be analyzed in step S50, the hybridization of the nucleic acid (step S60) proceeds. The hybridization of the nucleic acid S60 according to the example of the present invention does not include the known prehybridization, i.e., the areas of the substrate where the nucleic acid to be analyzed has not been fixed will be not blocked with a blocking reagent. The step S60 includes the step S62 of adding a solution containing a nucleic acid probe on the substrate for hybridization and base pairing the nucleic acid probe with the nucleic acid to be analyzed thereon; and the step S62 of removing the nucleic acid probe which has not been bonded to the nucleic acid to be analyzed. Finally, in step S40, the hybridization signal is detected in a manner of coloring detection method S41, radiograph detection method S42, chemiluminescence detection method S43, and photoelectric detection method S44, but the detection method is not limited thereto.

Figure 3:
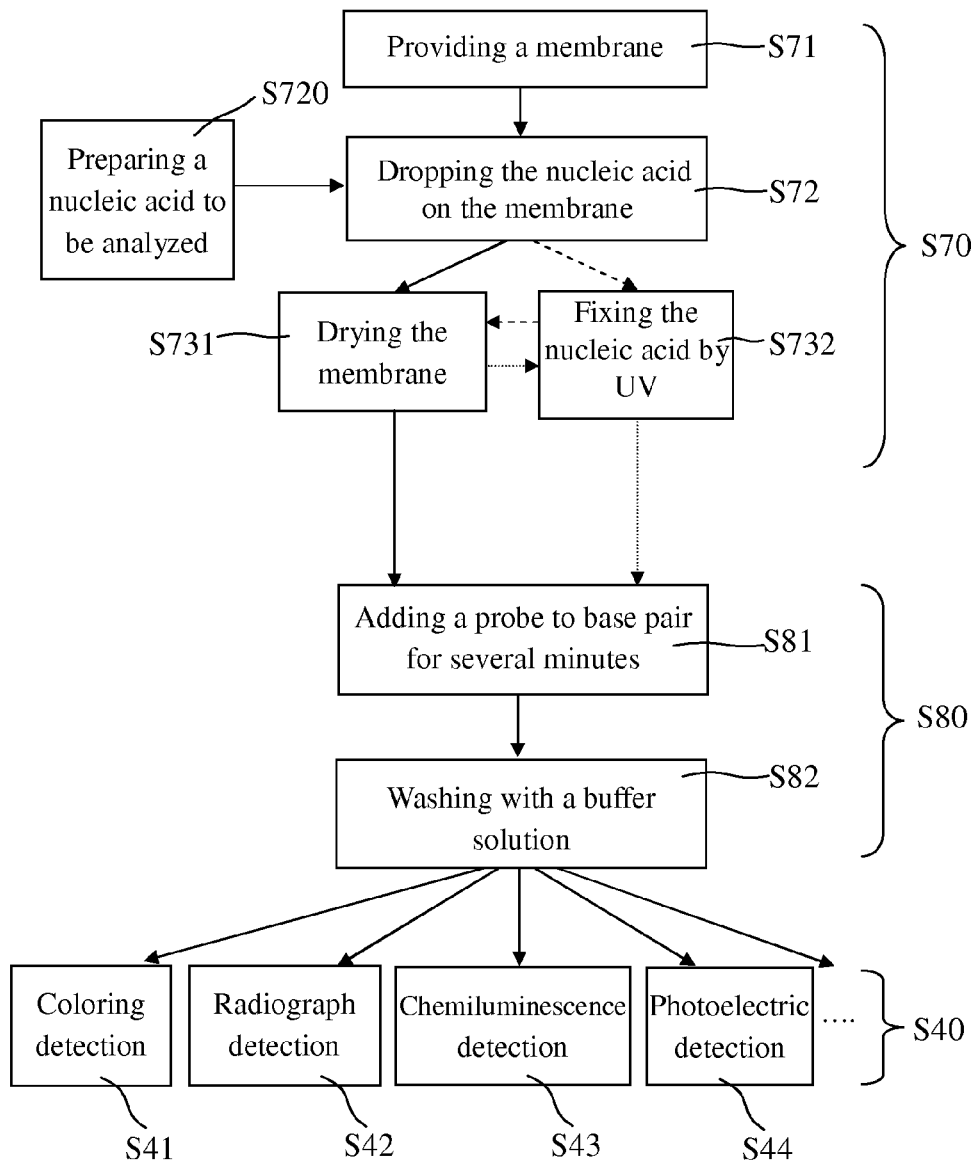
FIG. 3 is a flow chart showing a second embodiment of the present invention.

Referring to FIG. 3 which is a flow chart showing a second embodiment of the present invention, the blotting method for rapidly analyzing nucleic acid according to the embodiment of the present invention includes the steps of the treatment of the nucleic acid to be analyzed S70, the hybridization of the nucleic acid S80 and the detection of the hybridization signal S40. The nucleic acid to be analyzed is firstly transferred to the substrate, fixed thereon, and directly hybridized and paired without the step of prehybridization, and finally the hybridization signal is detected to finish the procedures of the blotting method for analyzing the nucleic acid of the present invention. The steps of this embodiment will be described in the way of the following examples.

EXAMPLE 1

The Treatment of the Nucleic Acid to be Analyzed

In the treatment of the nucleic acid to be analyzed (step S70), a membrane being able to absorb the nucleic acid to be analyzed was provided in step S71; the nucleic acid to be analyzed which was prepared in step S720 was added to the membrane in step S72; and then the nucleic acid to be analyzed was fixed on the membrane by drying in step S731 or by UV radiation in step S732. After step S732, the membrane is further subjected to the step S731 to be dried. Alternatively, the membrane was firstly radiated by UV in step S732 and then subjected to the step S731 to be dried.

The membrane provided in step S71 may be the traditional nylon membrane or nitrocellulose membrane, but is not limited thereto. The nylon membrane may have positive charge or have no charge, and absorbed more than 400 82 g/cm$^2$ nucleic acid, while nitrocellulose membrane absorbed 75 to 110 μg/cm$^2$ nucleic acid. The pores of the nylon membrane and nitrocellulose membrane may have a diameter of 0.1 to 50 μm, and preferably 0.2 to 0.45 μm. A diameter may be suitably selected according to the molecular weight of the nucleic acid to be analyzed, and becomes larger as the nucleic acid is larger.

In step S720, the nucleic acid to be analyzed was prepared by the known nucleic acid extraction and purification techniques. The nucleic acid to be analyzed is a nucleic acid sample which is to be determined whether having the required gene sequence or DNA/RNA fragment, and thus the method of the present invention can be applied in the analysis of DNA or RNA. The DNA extracted and then purified can be dissolved in a TE buffer solution (10 mM Tris-HCl, pH 8.0; 1 mM EDTA), while the RNA can be dissolved in a sterile water from which the RNase has been removed for use.

Either the DNA sample or the RNA sample has to be in the state of single chain in order to pair with the probe of single chain, and thus the denaturation is required in the known method. The DNA sample may be denatured by adding a multiple of 0.1 volume of 1 N NaOH into the DNA solution prepared above, reacting at 37° C. for 5 minutes, placing the resultant solution on the ice, and then adding a multiple of 0.1 volume of 2 M ammonium acetate (pH 7.0) thereto. The RNA sample may be denatured by adding 100% formamide (the final concentration being 50%), 37% formaldehyde (the final concentration being 50%) and 20 folds SSC solution (the final concentration being 100%) into the RNA solution prepared above, reacting at 68° C. for 15 minutes, placing the resultant solution on the ice, and then adding a multiple of 2 volume of 20 folds SSC solution thereto. However, the present inventor found that the sample could be denatured by heating at a high temperature or UV radiation in steps S731 and S732 (referring to the description below), and the denaturation step was not needed. Accordingly, there was no the process of denaturation, and thus the agents, solution and time for such step was saved.

After being prepared, the nucleic acid to be analyzed was dropped on the membrane in step S72. In this example, the nucleic acid to be analyzed was directly dropped on the dry membrane without the known process of soaking the membrane. This is because that, compared with a wet membrane, the nucleic acid probe solution could be quickly attracted by the capillarity generated by the fine pores of the dry membrane, and thus the time, device, solution and agents for the treatment of the nucleic acid to be analyzed in step S70 could be further lowered. The amount of the dropped nucleic acid to be analyzed could be calculated according to the absorption ability of the membrane, and was generally 0.5 to 2 μg/cm$^2$, preferably 1 μg/cm$^2$, but it was not limited thereto.

Figure 1:
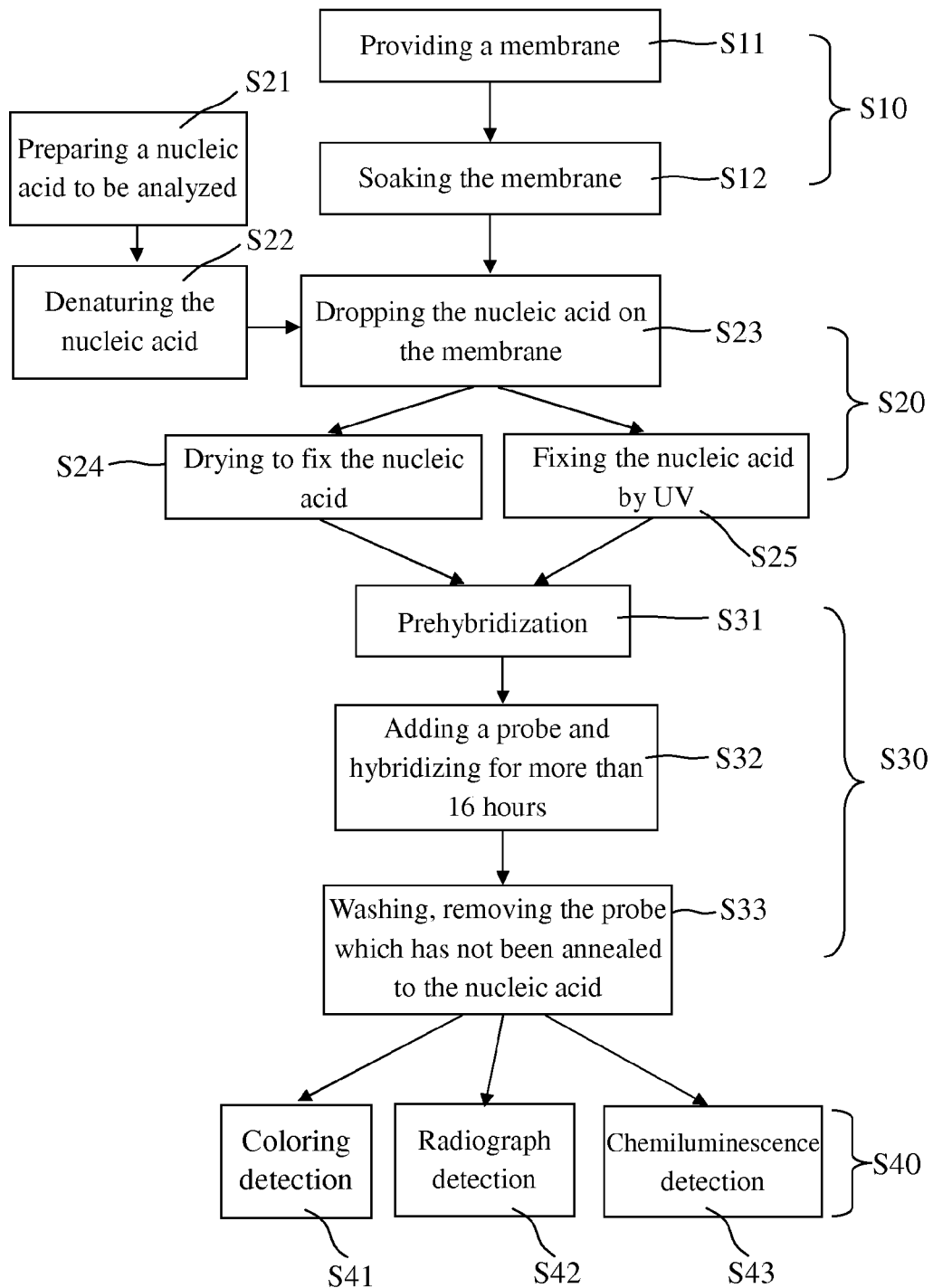
FIG. 1 is a flow chart showing the known dot blotting method for analyzing the nucleic acid.

After step S72, the membrane was dried in step S731 by drying the membrane at a temperature of 80° C. to 130° C., preferably 90° C. to 110° C., for 1 to 10 minutes, but the drying method was not limited thereto. The nucleic acid to be analyzed was absorbed and fixed on the membrane, however, in order to further strengthen the bonding force thereof, step S732 proceeded by exposing the membrane under UV of 2 to 5 J/cm$^2$ at 254 nm for 5 to 10 minutes. In addition, the membrane may be first exposed to the UV in step S732, and then dried in step S731. In step of S731 or S732, the nucleic acid to be analyzed could be denatured by the heating or UV radiation, and thus the above step of denaturing the nucleic acid to be analyzed was not needed. In the treatment (step S70) of the nucleic acid to be analyzed of the example of the present invention, the known step S12 of soaking the membrane, step S22 of denaturing the nucleic acid to be analyzed, and step S24 of drying and fixing the nucleic acid to be analyzed were not needed (referring to FIG. 1), and thus the procedure of the blotting method for analyzing the nucleic acid was simplified, and the agents, solution and time for those steps were also lowered.

EXAMPLE 2

The Hybridization of the Nucleic Acid

After being absorbed on the membrane, the nucleic acid to be analyzed was then hybridized in step S80. In general, the nucleic acid to be analyzed has not been fixed on some areas of the membrane where the nucleic acid can be still absorbed, and if these areas are not blocked, the added probe which is also nucleic acid will be non-specifically bonded to these areas of the membrane. Accordingly, in the prior art, the prehybridization was indispensably done before the hybridization to lower the background noise of the hybridization signal.

However, in the present invention, the membrane absorbing the nucleic acid to be analyzed was dried, and thus when the nucleic acid probe solution was added thereto, it could be quickly attracted by the capillarity generated by the fine pores of the membrane. Then the nucleic acid probe found the complementary nucleic acid to be analyzed by Brown Movement in rather a short time, and finished the hydrogen bonding of the bases thereof in tens of seconds. During the base pairing, the nucleic acid probe was hydrogen bonded more quickly with the nucleic acid to be analyzed than the membrane, the bonding force between the nucleic acid probe is stronger than the absorbing force between the nucleic acid probe and the membrane because the nucleic acid probe was not subjected to the process of drying the nucleic acid to be analyzed, and the absorbing force between the nucleic acid to be analyzed is stronger than that between the nucleic acid probe and the membrane. Moreover, unlike the giant molecule of the nucleic acid to be analyzed, the nucleic acid probe as a relatively small molecule can not be trapped in the pores of the membrane, and thus the nucleic acid probe which is non-specifically bonded to the membrane can be easily to remove in the subsequent washing, resulting in the hybridization of low background noise. The above is the reason that the prehybridization for blocking is not needed. As a result, in the example of the present invention, the prehybridization step was not needed, and thus the procedure required for the known techniques was simplified, and the agents, solution and time for the step were also lowered.

Accordingly, in step S80 of hybridizing the nucleic acid according to the present invention, the step S81 of base pairing was directly performed by preparing nucleic acid probe marked with the detecting molecules, dropping an appropriate amount of nucleic acid probe on the surface having absorbed the nucleic acid to be analyzed, and reacting them at a temperature of 40° C. to 70° C., preferably 46° C. to 56° C., for 2 to 5 minutes. The reacting temperature could be adjusted according to the Tw (washing temperature) value of the nucleic acid probe molecule, but was not specially limited. Since the membrane was dry upon dropping the nucleic acid to be analyzed, the solution of the nucleic acid to be analyzed could be quickly absorbed by the membrane, and then the membrane was dried again. So, when the nucleic acid probe solution was added thereto, it could be quickly attracted by the capillarity generated by the fine pores of the membrane and found the complementary nucleic acid to be analyzed by Brown Movement. In addition to the negative pressure force generated by the capillarity of the membrane, the nucleic acid probe could also be entered quickly inside of the membrane by applying outer force utilizing the pressure difference. It could be achieved by vacuuming on the other side of the membrane to form a negative pressure to make the nucleic acid probe sucked into the substrate, or by pressuring to push the nucleic acid probe into the inside of the substrate. However, the exemplary methods were illustrative and not limited thereto.

According to the relation $T=d^2/D$ of diffusing time (T), diffusing distance(d) and diffusing coefficient (D), when a DNA (diffusing coefficient being $4\times10^{-11}$ m$^2$/sec) having 30 nucleotides (30-mer) moves in the pores of the membrane, the diffusing time is only 0.6 second, and just 25 seconds for 5000-mer DNA (diffusing coefficient being $1\times10^{-12}$ m$^2$/sec). Accordingly, the nucleic acid probe spreading in the pores of the membrane could quickly finish the process of diffusing and finish the process of base pairing in less than one minute in each pore. As a result, the long time for the nucleic acid probe to slowly spread from the outside to the surface of the wet membrane and then spread from the surface to the inside of the membrane was shortened, the nucleic acid probe could quickly enter the membrane cellulose, and the hybridization could be finished rapidly. So the hybridization time was largely shortened, and the step S81 could be finished in several minutes.

After the step S81 of base pairing, the step S82 of washing proceeded to wash off the unpaired nucleic acid probe. As described above, the nucleic acid probe pairs with the nucleic acid to be analyzed rather quickly, and the bonding force between the nucleic acid probe is stronger than the absorbing force between the nucleic acid probe because the nucleic acid probe was not subjected to the process of drying the nucleic acid to be analyzed. As a result, the nucleic acid probe which is non-specifically bonded to the membrane can be easily removed during washing, resulting in the hybridization of low background noise. However, in order to prevent nucleic acid to be analyzed having been fixed from being removed during washing, it is preferred to wash with a buffer solution of low ionic strength for several minutes, generally 3 to 7 minutes and preferably 4 to 6 minutes. It could be washed with a 0.05 to 0.15 fold SSC solution as a buffer solution of low ionic strength at the ambient temperature for twice, and each time for 4 to 6 minutes. In case of the nitrocellulose membrane, 0.05% to 0.15% (w/v) of SDS may be further added for washing. Preferably, the concentration of SSC solution was 0.1 fold, and the concentration of the SDS solution was 0.1% (w/v).

As a result, in the step S80 of hybridizing the nucleic acid of the example according to the present invention, the known prehybridization (referring to step S31 in FIG. 1) was not needed, the hybridization time was shortened from tens of hours to several minutes, and the time for the washing (step S33) was also shortened to several minutes. Accordingly, in the step S80 of the present invention, the reaction time, and the cost of the related agents and solution were largely shortened.

As described above, according to the blotting method for rapidly analyzing nucleic acid of the present invention, either the treatment of the nucleic acid to be analyzed (step S70) or the nucleic acid hybridization (step S80) could be finished in several minutes, the time for all the above steps is just 30 to 45 minutes, and thus the time and material cost of the blotting method for analyzing the nucleic acid is largely and efficiently improved compared with the traditional method in which at least two days were needed.

In the above examples, the nucleic acid to be analyzed is firstly transferred (dropped) to and fixed on the substrate (the membrane), and then the nucleic acid probe is added for the hybridization. Optionally, the nucleic acid probe is firstly transferred (dropped) to and fixed on the substrate (the membrane), and then the nucleic acid to be analyzed is added for the hybridization. Since the nucleic acid probe is generally a nucleic acid fragment marked with detecting molecules such as fluorescent molecules, coloring molecules and the like, if the nucleic acid probe is firstly absorbed on the substrate (the membrane), all the nucleic acid probe will be still absorbed thereon. Therefore, in this case, the general indication-type probe and detection method such as coloring, fluorescence, radiography and the like is not suitable because of no distinguishing, and impedance detection method, capacitance detection method, resistance detection method, or electrochemical detection method may be used.

After washing, only the nucleic acid probe pairing with the nucleic acid to be analyzed remains on the hybridized membrane, and then the step S40 may proceed to detect the hybridization signal. A suitable detection method may be selected according to the marker of the probe. For the detection method, there are many commercial kits which can be used for coloring or other presenting reactions and also contain agents and solution for preparing the probe. Concerning the coloring detection method S41, the coloring system using the digoxigenin (DIG) is currently most used, in which an anti-DIG antibody bonded with alkaline dephosphorylase is reacted with a coloring receiver such as nitroblue tetrazolium (NBT), 5-bromo-4-chloro-3-indolyl phosphate (BCIP) or CSPD® for coloring. Base on the description herein, it will be understood by those skilled in the art that the nucleic acid probe may be marked with biotin during the preparation thereof, and the react with streptavidin and enzyme. In addition, radiography detection method S42 marking the radioactive element $^{32}$P or $^{35}$S, or chemiluminescence detection method S43 using HEX, Cy3 and Cy5 may also be useful. Other detection method may also be useful such as a photoelectric detection method S44 including impedance detection, capacitance detection, resistance detection, and electrochemical detection, and mass detection or weight detection method. However, the detection method is not limited thereto.

EXAMPLE 3

Analysis on the Time for Drying and Fixing the Nucleic Acid

A dry nylon membrane having pores of 0.45 μm in diameter was provided, and round pieces thereof having a diameter of 6 mm (area of about 28 mm$^2$) were prepared by using a paper puncher. Subsequently, a solution containing the nucleic acid to be analyzed was directly dropped on the center of each nylon membrane piece (meantime deionized water was dropped on one nylon membrane piece as control), and then the nylon membrane pieces were place on a heater and dried at a temperature of 100° C. for various time to analyze the fixation difference of the nucleic acid to be analyzed in case of different fixing time.

The nylon membrane having the nucleic acid to be analyzed fixed thereon was washed in a buffer solution of low ion strength (for example, 0.1 fold SSC+0.01% (w/v) SDS) 5 times to wash off the unfixed nucleic acid to be analyzed, 10 minutes for each time. Subsequently, a solution containing the nucleic acid probe marked with fluorescent molecules was dropped on the center of each nylon membrane piece, and after base pairing at 46° C. for 10 minutes, the nylon membrane pieces were washed in a buffer solution (0.1 fold SSC+0.01% (w/v) SDS) 3 times, 10 minutes for each time. Finally, the nylon membranes of different fixing time are detected to determine the fluorescence.

Figure 4:
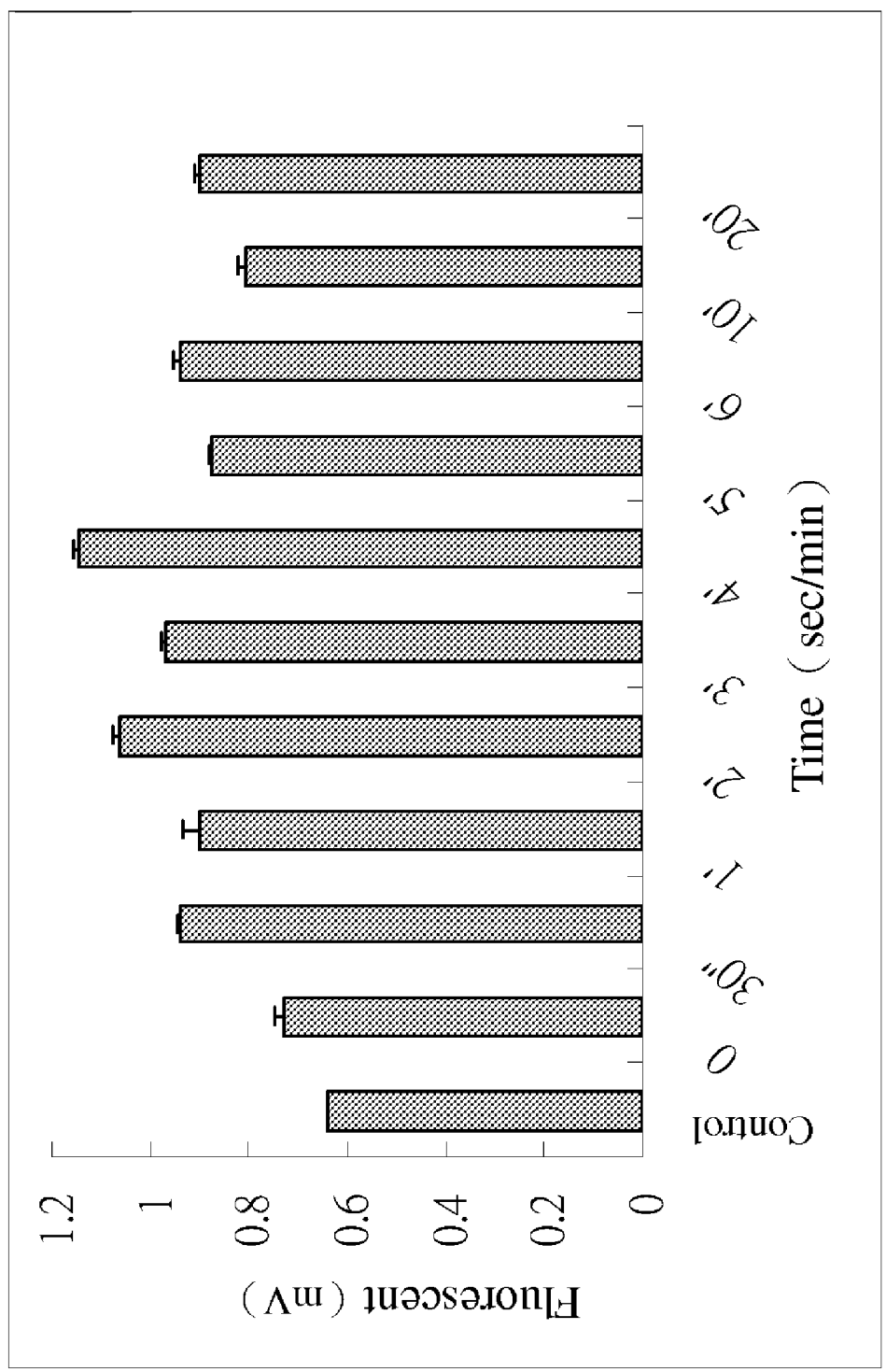
FIG. 4 shows the result of comparing the fixation of nucleic acid under various fixing time, in which the abscissa represents the drying and fixing time, and the ordinate represents the fluorescent strength.

Referring to FIG. 4, it shows the result of comparing the fixation of nucleic acid under various fixing time. In FIG. 4, the abscissa represents the drying and fixing time, and the ordinate represents the fluorescent strength. It could be apparently from the drawing that when the drying and fixing time is more than about 30 seconds to 1 minute, the fluorescent strength observably differs from that of the control. Therefore, in the present invention, the drying and fixing can be finished in 30 seconds to 1 minute.

EXAMPLE 4

Analysis on the Time for Base Pairing

A dry nylon membrane having pores of 0.45 μm in diameter was provided, and round nylon membrane pieces thereof having a diameter of 6 mm (area of about 28 mm$^2$) were prepared by using a paper puncher. Subsequently, a solution containing the nucleic acid to be analyzed was directly dropped on the center of each nylon membrane piece (meantime deionized water was dropped on one nylon membrane piece as control), and then the nylon membrane pieces were place on a heater and dried at a temperature of 100° C. for 10 minutes. Thereafter, a solution containing the nucleic acid probe marked with fluorescent molecules was dropped on the center of each nylon membrane piece, and after base pairing at 46° C. for various time, the nylon membrane pieces were washed in a buffer solution (0.1 fold SSC+0.01% (w/v) SDS) 3 times, 10 minutes for each time. Finally, the nylon membranes of different base pairing time are detected to determine the fluorescence.

Figure 5:
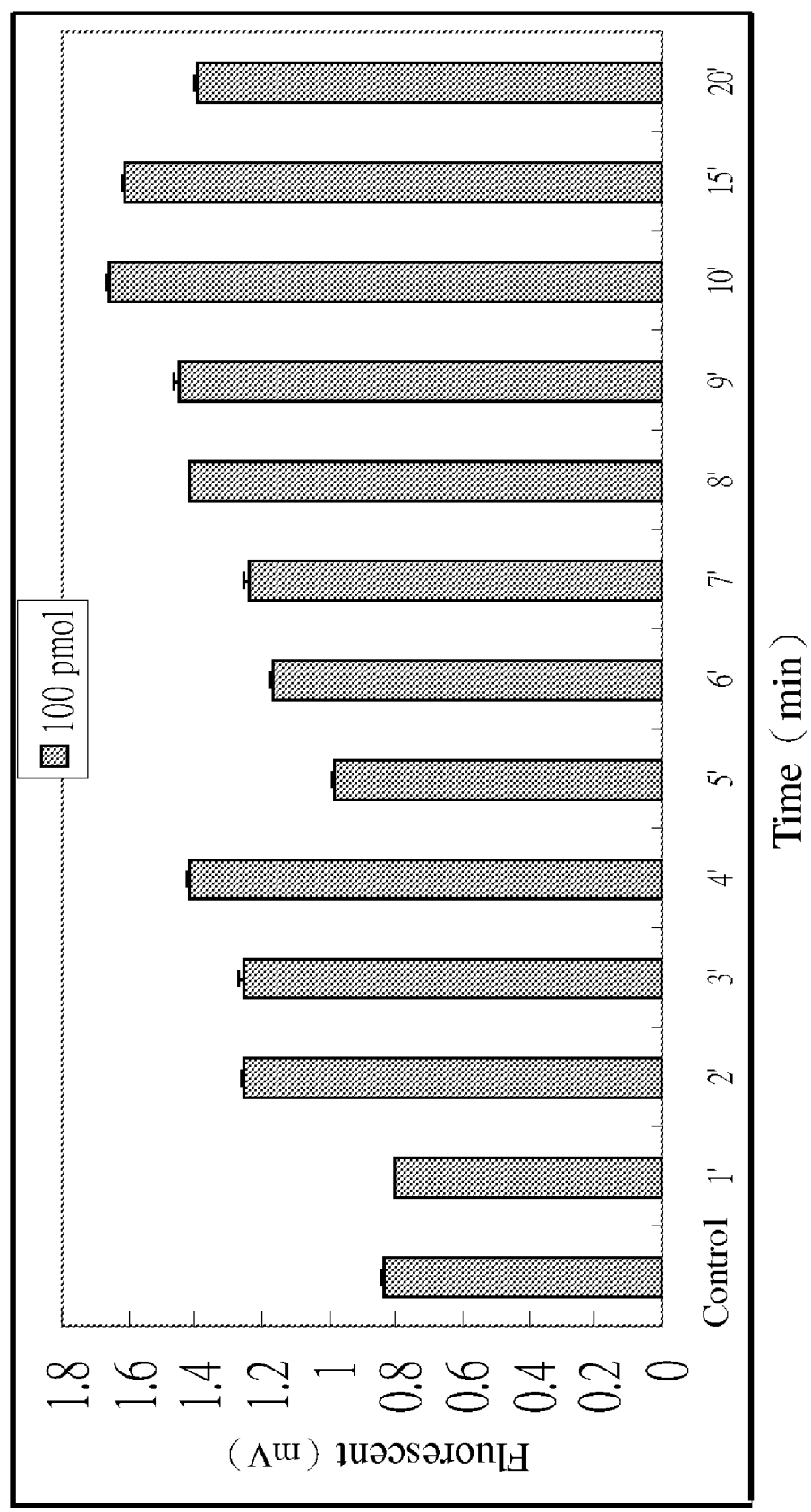
FIG. 5 shows the result of comparing the base pairing under various reacting time, in which the abscissa represents the base pairing time, and the ordinate represents the fluorescent strength.

Referring to FIG. 5, it shows the result of comparing the base pairing under various reacting time. In FIG. 5, the abscissa represents the base pairing time, and the ordinate represents the fluorescent strength. It could be apparently from the drawing that when the base pairing time is more than about 2 minutes, the fluorescent strength observably differs from that of the control. Therefore, in the present invention, the base pairing can be finished in 2 minutes.

EXAMPLE 5

Using a Microfluidics to Analyze the Nucleic Acid by Blotting

A microfluidics is provided, and a 4×7 mm nylon membrane having pores of 0.45 μm in diameter is installed therein. 10 μl (10 ng) of E. coli DNA, E. tarda DNA, and deionized water (as control) are, filled respectively by using a syringe connected with a connective tube, transferred to the nylon membrane and absorbed thereon. Thereafter, the microfluidics is dried on a heater of 120° C. for 10 minutes to fix the nucleic acid to be analyzed on the nylon membrane.

Then the nucleic hybridization is performed by filling a nucleic acid probe (the nucleic acid probe is only complementary to the DNA of E. tarda) marked with fluorescent molecules in the nylon membrane through microchannels with pressure, placing the microfluidics on a heater of 46° C. to perform the hybridization reaction for 2 minutes. Thereafter, the nylon membrane contained in microfluidics is washed by continuously filling a buffer solution (0.1 fold SSC+0.01% (w/v) SDS) 3 times, 2 minutes and 1 ml for each time. The fluorescence is detected after each wash.

Figure 6:
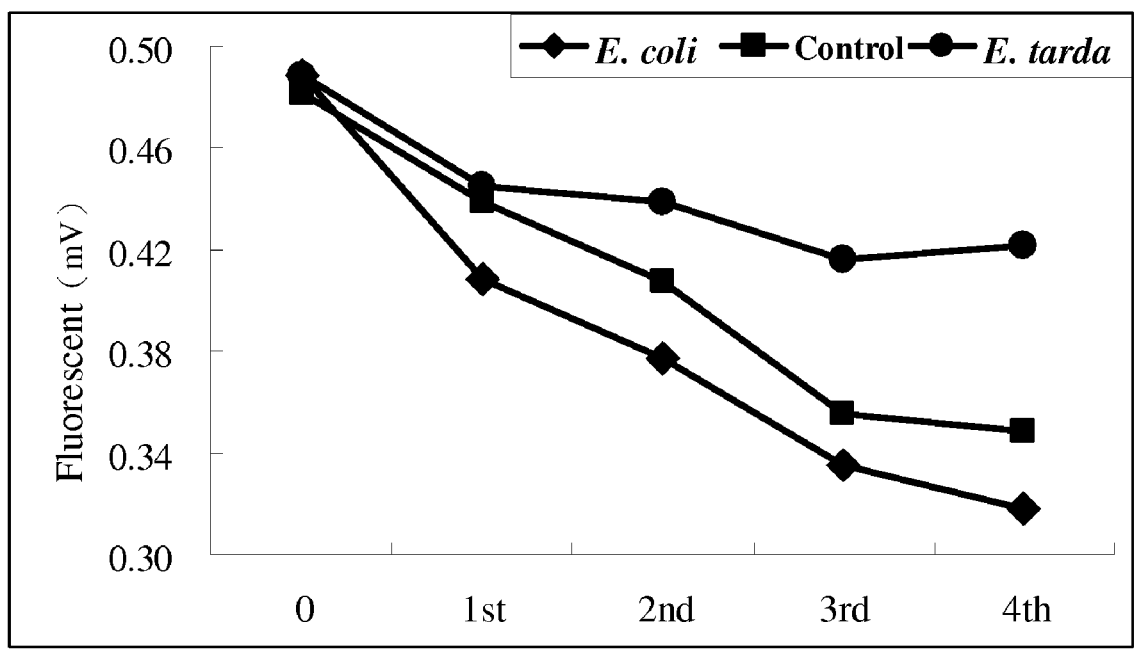
FIG. 6 shows the hybridization result of the blotting method for analyzing the nucleic acid by using a microfluidics according to this example of the present invention, in which the abscissa represents the washing times, the ordinate represents the fluorescent strength, [♦] represents E. coli DNA, [■] represents the control of only probe nuclei acid, and [●] represents E. tarda DNA.

Referring to FIG. 6, it shows the hybridization result of the blotting method for analyzing the nucleic acid by using a microfluidics according to this example of the present invention. In FIG. 6, the abscissa represents the washing times, and the ordinate represents the fluorescent strength. [♦] represents E. coli DNA, [■] represents the control of only probe nuclei acid, and [●] represents E. tarda DNA. It could be apparently from the drawing that the fluorescent strength decreases as the washing times increase, of which the reason is that the nucleic acid probe is gradually washed off. In addition, since the nucleic acid probe can not pair with E. coli DNA, the detected fluorescent strength is the lowest. However, its fluorescent strength is higher than the control of only nucleic acid probe, because the E. coli DNA is firstly absorbed on the nylon membrane and filled in the pores of nylon membrane, while the nucleic acid probe as background is added later and will be difficult to be absorbed on the nylon membrane. In contrast, for the control in which no nucleic acid to be analyzed is absorbed, the nucleic acid probe can be absorbed randomly, the absorbing ratio increases, and thus the fluorescent strength is high. However, it could be seen form the result that, after washing twice, it is distinguishable whether the nucleic acid probe pair with the nucleic acid to be analyzed, and after washing for 3 times, it is remarkably distinguishable.

What is claimed is:

1. A blotting method without the process of blocking for analyzing nucleic acid comprising the following steps:
   (1) providing a substrate having a plurality of pores;
   (2) transferring a nucleic acid to be analyzed to the substrate and allowing absorption of the nucleic acid by the substrate;
   (3) fixing the nucleic acid to be analyzed on the substrate, and the substrate is a dry substrate;
   (4) adding a solution containing a nucleic acid probe on the dry substrate of step (3) to base-pair the nucleic acid probe with the nucleic acid to be analyzed thereon for two or more minutes, without blocking the areas of the substrate where the nucleic acid to be analyzed has not been fixed;

(5) removing the nucleic acid probe which has not been annealed to the nucleic acid to be analyzed of step (4); and (6) detecting the hybridization signal on the substrate having been subjected to step (5), wherein in step (3), the substrate is dried at a temperature of 80° C. to 130° C. to fix the nucleic acid to be analyzed on the substrate and the drying time is 1 to 10 minutes.

2. The blotting method for analyzing nucleic acid according to claim 1, wherein the substrate in step (1) is also dry.

3. The blotting method for analyzing nucleic acid according to claim 1, wherein the substrate in step (1) is a membrane.

4. The blotting method for analyzing nucleic acid according to claim 3, wherein the substrate is a nylon membrane or nitrocellulose membrane.

5. The blotting method for analyzing nucleic acid according to claim 1, wherein the pores of the substrate have a diameter of 0.1 to 50 μm.

6. The blotting method for analyzing nucleic acid according to claim 1, wherein in step (3), the substrate is radiated with ultraviolet light to fix the nucleic acid to be analyzed on the substrate.

7. The blotting method for analyzing nucleic acid according to claim 6, wherein after step (3), the substrate having the nucleic acid to be analyzed fixed thereon is further dried.

8. The blotting method for analyzing nucleic acid according to claim 1, wherein in step (4), the base pairing time is 2 to 5 minutes.

9. The blotting method for analyzing nucleic acid according to claim 1, wherein in step (5), a buffer solution is used for washing off the nucleic acid probe that has not been annealed to the nucleic acid to be analyzed.

10. The blotting method for analyzing nucleic acid according to claim 9, wherein in step (5), the buffer solution having low ionic strength, wherein the buffer solution comprises a 0.05 to 0.15 fold standard sodium citrate.

11. The blotting method for analyzing nucleic acid according to claim 10, wherein in step (5), the buffer solution of low ionic strength further comprises a sodium dodecyl sulfate of 0.05% to 0.15%(w/v).

12. The blotting method for analyzing nucleic acid according to claim 11, wherein in step (5), for the buffer solution of low ionic strength, the washing time is 3 to 6 minutes.

13. A blotting method for analyzing nucleic acid comprising the following steps:

(1) providing a dry substrate which has a plurality of pores and is dry;

(2) transferring a nucleic acid to be analyzed to the dry substrate and allowing absorption of the nucleic acid by the substrate without pre-wetting;

(3) fixing the nucleic acid to be analyzed on the substrate;

(4) interacting a solution containing a nucleic acid probe with the substrate of step (3) at a temperature of 40° C. to 70° C., to base-pair the nucleic acid probe with the nucleic acid to be analyzed thereon for two or more minutes;

(5) washing the substrate of step (4) with a buffer solution to remove the nucleic acid probe which has not been annealed to the nucleic acid to be analyzed; and (6) detecting the hybridization signal on the substrate having been subjected to step (5).

14. A blotting method for analyzing nucleic acid comprising the following steps:

(1) providing a substrate having a plurality of pores;

(2) transferring a nucleic acid probe to the substrate and allowing absorption of the nucleic acid probe by the substrate without pre-wetting;

(3) fixing the nucleic acid probe on the substrate, and then drying the substrate again into a dry substrate;

(4) interacting a solution containing a nucleic acid to be analyzed with the dry substrate of step (3) at a temperature of 40° C. to 70° C., to base-pair the nucleic acid probe with the nucleic acid to be analyzed thereon for two or more minutes;

(5) washing the substrate of step (4) with a buffer solution to remove the nucleic acid to be analyzed which has not been annealed to the nucleic acid probe; and (6) detecting the hybridization signal on the substrate having been subjected to step (5).

15. A blotting method for analyzing nucleic acid comprising the following steps:

(1) providing a substrate having a plurality of pores;

(2) transferring a nucleic acid to be analyzed to the substrate and allowing absorption of the nucleic acid by the substrate;

(3) fixing the nucleic acid to be analyzed on the substrate, and the substrate is dry;

(4) adding a solution containing a nucleic acid probe on the dry substrate of step (3) by using a pressure difference generated by a capillarity of the substrate, entering it in the substrate, and base pairing the nucleic acid probe with the nucleic acid to be analyzed thereon for two or more minutes;

(5) washing the substrate of step (4) with a buffer solution to remove the nucleic acid probe which has not been annealed to the nucleic acid to be analyzed; and (6) detecting the hybridization signal on the substrate having been subjected to step (5).

16. The blotting method for analyzing nucleic acid according to claim 15, wherein in step (4), the pressure difference is resulted by vacuuming on a first side of the substrate to form a negative pressure to make the nucleic acid probe sucked into a second side of the substrate, or by pressuring to push the nucleic acid probe into at least one of the first and second sides of the substrate.

* * * * *